United States Patent
Galdi et al.

(12)

(10) Patent No.: US 7,022,316 B2
(45) Date of Patent: Apr. 4, 2006

(54) NON-PILLING UV-PHOTOPROTECTING SUNSCREEN COMPOSITIONS

(75) Inventors: Angelike A. Galdi, Westfield, NJ (US); Isabelle Hansenne, Westfield, NJ (US); Donald W. Rick, Dumont, NJ (US)

(73) Assignee: L'Oreal, Paris (FR)

( * ) Notice: Subject to any disclaimer, the term of this patent is extended or adjusted under 35 U.S.C. 154(b) by 343 days.

(21) Appl. No.: 10/372,330

(22) Filed: Feb. 25, 2003

(65) Prior Publication Data

US 2004/0166070 A1  Aug. 26, 2004

(51) Int. Cl.
*A61K 7/42* (2006.01)
*A61K 7/44* (2006.01)
*A61K 7/00* (2006.01)

(52) U.S. Cl. ............... 424/59; 424/60; 424/400; 424/401

(58) Field of Classification Search ............... 424/59, 424/60, 400, 401
See application file for complete search history.

(56) References Cited

U.S. PATENT DOCUMENTS 5,618,522 A * 4/1997 Kaleta et al. .............. 424/60
2003/0021847 A1  1/2003 Baxter et al.

FOREIGN PATENT DOCUMENTS

WO  WO 03/082237 A2  10/2003

OTHER PUBLICATIONS

Boswell, "Skin, Sun and Hair Care Offer Fertile Ground for Innovation", *Chemical Market Reporter*, Dec. 3, 2001, 2 pages.
Machine Translation of Göppel et al., "Water Proof Cosmetic and Dermatological Sun Protecting Formulations Containing Acetylated Stearic Acid Esters", WO 03/082237, Published Oct. 9, 2003.
Poster Presentation by ISP About Allianz OPT, Presented in Dec. 2001 at the Society of Cosmetic Chemists Meeting in New York, 2 pages.

* cited by examiner

*Primary Examiner*—Shelley A. Dodson
(74) *Attorney, Agent, or Firm*—Buchanan Ingersoll, P.C.

(57) ABSTRACT

Topically applicable, non-pilling UV-photoprotecting cosmetic/dermatological sunscreen compositions, advantageously alcoholic sunscreen gels, well suited for UV-photoprotecting human skin and/or hair against the damaging and deleterious effects of ultraviolet irradiation, contain an effective amount of at least one UV-A and/or UV-B screening agent and an effective non-pilling amount of an acrylates/$C_{12-22}$ alkylmethacrylate copolymer, preferably a tetrapolymer of methacrylic acid, methyl methacrylate, butyl acrylate and cetyl-eicosinyl methacrylate, formulated into a topically applicable, cosmetically/dermatologically acceptable vehicle, diluent or carrier therefor.

17 Claims, No Drawings

NON-PILLING UV-PHOTOPROTECTING SUNSCREEN COMPOSITIONS

BACKGROUND OF THE INVENTION

1. Technical Field of the Invention

The present invention relates to novel topically applicable cosmetic/dermatological compositions for the UV-photoprotection of human skin and/or hair against the damaging effects of UV-photoprotection, in particular solar radiation, and to the use of same for the aforesaid cosmetic/dermatological indications.

This invention more specifically relates to topically applicable UV-A and/or UV-B sunscreen compositions, most notably alcoholic sunscreen gels, that are waterproof, have pleasant aesthetics and, characteristically, exhibit virtually no pilling. The subject compositions are well suited as "sport" products and comprise an effective non-pilling amount of a tetrapolymer of methacrylic acid, methyl methacrylate, butyl acrylate and cetyl-eicosinyl methacrylate.

2. Description of the Prior Art

It is well known to this art that light radiation of wavelengths of from 280 nm to 400 nm promotes tanning of the human epidermis, and that irradiation of wavelengths of from 280 nm to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the case of sensitive skin or a skin which is continually exposed to solar radiation.

UV-A rays cause, in particular a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen our UV-A radiation.

A wide variety of cosmetic compositions intended for the photoprotection (UV-A and/or UV-B) of human skin is known to this art.

These photoprotective/sunscreen compositions are quite often oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

Alcohol based sunscreen gel compositions are ideal for sport applications because they are fast drying and non-greasy. Polymeric film-formers are incorporated into these formulations to ensure even coverage of the sunscreens and to assist in rendering the formulation water resistant. Nonetheless, many of the common film-forming polymers included in sunscreen formations are not soluble in ethanol (such as PVP/Eicosene copolymer).

Indeed, the standard film-former employed in ethanol based sunscreen products is Dermacryl® LT marketed by National Starch & Chemical Company (INCI Name: acrylates/octylacrylamide copolymner). This polymer is easily solubilized in ethanol, but a major drawback of this polymer is that it rubs off the skin during product application, leaving the polymer residue in clumps of small balls or the like, resembling pills, on the skin ("pilling"). This is aesthetically unattractive, and may reduce or eliminate the function of the film-former.

Too, it is believed that all other film-formers to date included in alcohol based sunscreen formulations produce pilling during application of the product.

Dermacryl® LT (CAS Number: 80570-62-3), for example, is a hydrophobic, high molecular weight carboxylated acrylic copolymer. It functions as a film-former in a broad range of cosmetic formulations, imparting waterproofing, increased occlusivity and decreased rub-off of actives. Unlike traditional film-formers used in skin care, Dermacryl® LT is said to have been specifically designed to provide the performance benefits of a film-former without leaving the characteristic tactile properties. It is a fine, white, free-flowing powder, essentially free of foreign material: % volatiles—3.0 maximum; acidity—2.20 to 2.70 meq/g.

A number of Dermacryl® LT sunscreen compositions is commercially available from National Starch & Chemical. These include:

| Daily UV Protection Cream (SPF ≈ 16) | | | |
|---|---|---|---|
| Ingredients | INCI Designation | % W/W | Supplier |
| Phase A | | | |
| Neo Heliopan AV | Octyl Methoxycinnamate | 7.50 | Haarmann & Reimer |
| Myrj 52S | PEG-40 Stearate | 1.00 | Uniqema |
| Cerasynt Q | Glyceryl Stearate SE | 2.00 | Van Dyk |
| Cetyl Alcohol | Cetyl Alcohol | 1.00 | |
| Emersol 132 | Stearic Acid T.P. | 3.00 | Emery |
| Tioveil FIN | Titanium Dioxide/ $C_{12-15}$ Alkyl Benzoate | 1.70 | Tioxide |
| Finsolv TN | $C_{12-15}$ Alkyl Benzoate | 5.00 | Finetex |
| DC 344 Fluid | Cyclomethicone | 3.00 | Dow Corning |
| DC 556 Fluid | Phenyl Trimethicone | 1.00 | Dow Corning |
| Abil B8852 | Dimethicone Copolyol | 1.00 | Goldschmidt |
| Phase B | | | |
| Deionized Water | Water (Aqua) | 32.80 | |
| Triethanolamine (99%) | Triethanolamine | 4.00 | Dow |
| Dermacryl LT | Acrylates/ Octylacrylamide Copolymer | 1.00 | National Starch |
| Neo Heliopan Hydro | 2-Phenylbenzimidazole-5-Sulfonic Acid | 4.00 | H&R |
| Carbopol 940 (2% Aq. Soln.) | Carbomer | 25.00 | B.F. Goodrich |
| Phase C | | | |
| Propylene Glycol | Propylene Glycol | 3.00 | |
| Dry-Flo PC | Aluminum Starch Octenylsuccinate | 3.00 | National Starch |
| Phase D | | | |
| Germaben IIE | Propylene Glycol (and) Diazolidinyl Urea (and) Methylparaben (and) Propylparaben | 1.00 | Sutton Labs |
| | | 100.00 | |

This product (supplier designation 7528-149A) is formulated as follows:

Phase B: Combine Triethanolamine (99%) and Deionized Water, heat to 60° C. Slowly sift in Dermacryl LT heat to 80° C. When complete, sift in Neo Heliopan Hydro and Carbopol 940, mix until complete.

Phase A: Combine and heat to 80° C. Add Phase A to Phase B at 80° C., mix for 15–30 minutes. Cool to 40° C. Slurry Dry-Flo PC in Propylene Glycol, add to Phase A and Phase B at 40° C., mix thoroughly. Add Phase D. Cool to room temperature and package.

Daily UV Protection Lotion (SPF ≈ 18)

| Ingredients | INCI Designation | % W/W | Supplier |
|---|---|---|---|
| Phase A | | | |
| Neo Heliopan AV | Octyl Methoxycinnamate | 7.50 | Haarmann & Reimer |
| Brij 76 | Stearate 10 | 1.00 | Uniqema |
| Cerasynt Q | Glyceryl Stearate SE | 1.50 | Van Dyk |
| Cetyl Alcohol | Cetyl Alcohol | 1.00 | |
| Emersol 132 | Stearic Acid T.P. | 1.50 | Emery |
| Tioveil FIN | Titanium Dioxide/ $C_{12-15}$ Alkyl Benzoate | 1.70 | Tioxide |
| Finsolv TN | $C_{12-15}$ Alkyl Benzoate | 5.00 | Finetex |
| DC 344 Fluid | Cyclomethicone | 3.00 | Dow Corning |
| DC 556 Fluid | Phenyl Trimethicone | 1.00 | Dow Corning |
| Abil B8852 | Dimethicone Copolyol | 0.50 | Goldschmidt |
| Phase B | | | |
| Deionized Water | Water (Aqua) | 40.30 | |
| Triethanolamine (99%) | Triethanolamine | 4.00 | Dow |
| Dermacryl LT | Acrylates/ Octylacrylamide Copolymer | 1.00 | National Starch |
| Neo Heliopan Hydro | 2-Phenylbenzimidazole-5-Sulfonic Acid | 4.00 | H&R |
| Carbopol 940 (2% Aq. Soln.) | Carbomer | 20.00 | B.F. Goodrich |
| Phase C | | | |
| Propylene Glycol | Propylene Glycol | 3.00 | |
| Dry-Flo PC | Aluminum Starch Octenyl succinate | 3.00 | National Starch |
| Phase D | | | |
| Germaben IIE | Propylene Glycol (and) Diazolidinyl Urea (and) Methylparaben (and) Propylparaben | 1.00 | Sutton Labs |
| | | 100.00 | |

This product (supplier designation 7528-149B) is formulated as follows:

Phase B: Combine Triethanolamine (99%) and Deionized Water, heat to 60° C. Slowly sift in Dermacryl LT heat to 80° C. When complete, sift in Neo Heliopan Hydro and Carbopol 940, mix until complete.

Phase A: Combine and heat to 80° C. Add Phase A to Phase B at 80° C., mix for 15–30 minutes. Cool to 40° C. Slurry Dry-Flo PC in Propylene Glycol, add to Phase A and Phase B at 40° C., mix thoroughly. Add Phase D. Cool to room temperature and package.

After Sun Lotion

| Ingredients | INCI Designation | % W/W | Supplier |
|---|---|---|---|
| Phase A | | | |
| Emersol 132 | Stearic Acid T.P. | 2.00 | Emery |
| Finsolv TN | $C_{12-15}$ Alkyl Benzoate | 6.50 | Finetex |
| Fancol CB | Cocoa Butter | 1.00 | Fanning |
| Lipovol WGO | Wheat Germ Oil | 1.00 | Lipo |
| Vitamin E Acetate-C | Tocopheryl Acetate | 0.50 | BASF |
| Cerasynt SD | Glyceryl Stearate | 2.00 | Van Dyk |
| Myrj 52S | PEG-40 Stearate | 1.00 | Uniqema |
| Phase B | | | |
| Deionized Water | Water (Aqua) | 59.30 | |
| Aloe Vera Gel 1:1 | Aloe Barbadensis Gel | 10.00 | Dr. Madis Labs |
| Pricerene 9088 | Glycerin | 3.00 | Uniqema |
| Carbopol 940 (2% Aq. Soln.) | Carbomer | 10.00 | B.F. Goodrich |
| Triethanolamine (99%) | Triethanolamine | 1.00 | Dow |
| Allantoin | Allantoin | 0.50 | Sutton Labs |
| Dermacryl LT | Acrylates/ Octylacrylamide Copolymer | 1.00 | National Starch |
| Phase C | | | |
| Germaben IIE | Propylene Glycol (and) Diazolidinyl Urea (and) Methylparaben (and) Propylparaben | 1.00 | Sutton Labs |
| Phase D | | | |
| Fragrance | Fragrance (Perfume) | 0.20 | |
| | | 100.00 | |

And this particular product (supplier designation 7661-23) is formulated as follows:

Combine Phase B, except for Dermacryl LT. Heat to 80° C. Slowly sift in Dermacryl LT, mix until complete. Combine Phase A, heat to 80° C. Add Phase A to Phase B at 80° C., mix for 30 minutes. Cool to 40° C., add Phase C and Phase D. Cool to room temperature and package.

The aforesaid phenomenon of pilling, however, remains a conspicuous disadvantage and drawback in the high SPF alcoholic sunscreen gel art.

SUMMARY OF THE INVENTION

It has now unexpectedly and surprisingly been determined that high SPF aesthetically pleasant and water resistant UV-A and/or UV-B sunscreen compositions that produce no pilling during product application are obtained by formulating therein an effective film-forming and non-pilling amount of an acrylates/$C_{12-22}$ alkylmethacrylate copolymer, in particular a tetrapolymer of methacrylic acid, methyl methacrylate, butyl acrylate and cetyl-eicosinyl methacrylate.

DETAILED DESCRIPTION OF BEST MODE
AND SPECIFIC/PREFERRED EMBODIMENTS
OF THE INVENTION

More particularly according to the present invention, preferred acrylates/$C_{12-22}$ alkylmethacrylate copolymers well suited for formulating the subject topically applicable cosmetic/dermatological sunscreen compositions are those tetrapolymers of methacrylic acid, methyl methacrylate, butyl acrylate and cetyl-eicosinyl methacrylate marketed by Rohm and Haas and ISP Technologies (an affiliate of International Specialities Products (ISP)) under the trademark Allianz OPT.

Allianz OPT is marketed as an emulsion at about 50% solids in water, preserved with 1% methyl paraben. Acute, phototoxicity, sensitization (RIPT) and photo-allergenicity test results have been favorable.

Also, Allianz OPT, having the appearance of a milky white aqueous dispersion, for example having a solids content on the order of 47–49%, a pH of from 5.0–6.5 and 250 ppm max of residual monomers, was specifically designed to provide structure to oil phases comprised mostly of organic sunscreens. It imparts structure by creating a large hydrophobic network throughout the oil phase. This network is said to be the result of both the intrinsic nature of the polymer and polymer-polymer interactions. The intrinsic nature of the polymer is a very hydrophobic, very high molecular weight, lightly crosslinked network structure. Each of these high molecular weight network structures can interact to create a super-molecular network which structure the oil phase. In this respect, it is very similar to aqueous based associative thickness.

Allianz OPT is thought to bind effectively to skin and resists being rubbed off. The Theological properties of a typical sunscreen oil phase (a mixture of octylmethoxy cinnamate, octylsalicylate, benzophenone-3 and octyl palmitate) with and without Allianz OPT have been examined. The system developed a significant viscosity, and exhibits a Theological profile typical of a structured liquid. Structured liquids initially resist flow when a shear stress is applied, until sufficient force overcomes the structure and induces flow. An oil phase without Allianz OPT behaves like a normal liquid, beginning to flow as soon as a shear stress is applied.

Thus, Allianz OPT oil phase technology provides an effective alternative to make sunscreen formulae very water resistant. Allianz OPT has also been recommended in low viscosity (sprayable) oil-in-water emulsions, nonionic emulsification systems, cold processes, water-soluble sunscreen actives, and alcohol-based products.

In the topically applicable non-pilling UV-photoprotecting sunscreen compositions according to the present invention, the active level of the acrylates/$C_{12-22}$ alkylmethacrylate copolymer, preferably the Allianz OPT tetrapolymer, advantageously ranges from 0.25% to 5.0% by weight. A range of from 1% to 5% by weight is the preferred. As Allianz OPT is an about 50% dispersion of polymer in water, it will be appreciated that 4% raw material is required to attain 2% active.

The subject topically applicable UV-A and/or UV-B sunscreen compositions, especially the alcoholic sunscreen gels, are formulated into the art recognized topically applicable, cosmetically/dermatologically acceptable vehicles, diluents or carriers therefor, for example in hydroxypropyl cellulose.

The subject compositions according to this invention contain an effective UV-photoprotecting amount of at least one UV-A and/or UV-B sunscreen, formulated into a topically applicable, cosmetically/dermatologically acceptable vehicle, diluent or carrier therefor.

By "UV-A and/or UV-B sunscreen" is intended any compound or any combination of compounds which, by mechanisms that are known per se of absorption and/or reflection and/or scattering of UV-A and/or UV-B radiation, prevents, or at least limits, the contact between such radiation and a surface (skin, hair) on which this or these compounds have been applied. Stated differently, these compounds may be UV-absorbing organic screening agents or inorganic (nano) pigments which scatter and/or reflect UV radiation, as well as mixtures thereof.

According to the present invention, the at least one UV-A and/or UV-B sunscreen may comprise one or more hydrophilic organic screening agents and/or one or more lipophilic organic screening agents and/or one or more mineral or inorganic (nano)pigments.

One preferred UV-photoprotecting agent according to the present invention is the dibenzoylmethane sunscreen avobenzone, or 4-(tert-butyl)-4'-methoxldibenzoylmethane, which is very well known to this art, is commercially available and is marketed, for example, under the trademark "PARSOL 1789" by Givaudan. It has the structural formula:

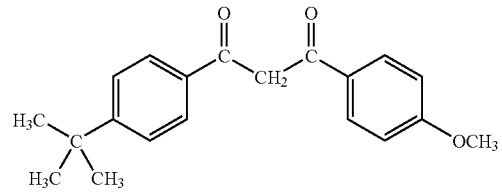

Sunscreens according to the present invention which are physical blockers reflect or scatter ultraviolet radiation. Typical examples of physical blockers include red petrolatum, titanium dioxide, and zinc oxide. These physical blockers have been employed in a variety of suspensions and particle sizes and are frequently included in cosmetic formulations. A review of physical blockers may be found at "Sun Protection Effect of Nonorganic Materials," by S. Nakada & H. Konishi, *Fragrance Journal*, Volume 15, pages 64–70 (1987), which is incorporated by reference herein.

Sunscreens according to this invention which are chemical absorbers, like avobenzone, actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

Classifying the chemical absorbers generally as UV-A or UV-B absorbers is accepted within the industry. However, a more precise classification is one based upon the chemical properties of the sunscreens. There are eight major classifications of sunscreen chemical properties which are discussed at length in "Sunscreens—Development, Evaluation and Regulatory Aspects," by N. Shaath et al., 2nd. Edition, pages 269–273, Marcel Dekker, Inc. (1997). This discussion, in its entirety, is incorporated by reference herein.

The sunscreens which may be formulated according to the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes, β,β-diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP-0,863,145, EP-0,517,104, EP-0,570,838, EP-0,796,851, EP-0,775,698, EP-0,878,469, EP-0,933,376, EP-0,893,119, EP-0,669,323, GB-2,303,549, DE-1,972,184 and WO-93/04665, also expressly incorporated by reference. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof. Other such representative sunscreens include the dimers derived from (alpha) alkyl styrene compounds, as described in DE 198 55 649, and the 4,4-diarylbutadienes, as described in EP-0,967,200 and DE 197 55 649.

A wide variety of sunscreens is described in U.S. Pat. No. 5,087,445, issued to Haffey et al. on Feb. 11, 1992; U.S. Pat. No. 5,073,372, issued to Turner et al. on Dec. 17, 1991; and Chapter VIII of *Cosmetics and Science and Technology* by Segarin et al., pages 189 et seq. (1957), all of which are incorporated herein by reference in their entirety.

Also preferred among those sunscreens which may be formulated into the compositions of the instant invention are those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

Similarly preferred sunscreens active in the UV-A and/or UV-B range include:
  p-aminobenzoic acid,
  oxyethylene (25 mol) p-aminobenzoate,
  2-ethylhexyl p-dimethylaminobenzoate,
  ethyl N-oxypropylene p-aminobenzoate,
  glycerol p-aminobenzoate,
  4-isopropylbenzyl salicylate,
  2-ethylhexyl 4-methoxycinnamate,
  methyl diisopropylcinnamate,
  isoamyl 4-methoxycinnamate,
  diethanolamine 4-methoxycinnamate,
  3-(4'-trimethylammunium)-benzyliden-bornan-2-one methylsulfate,
  2-hydroxy-4-methoxybenzophenone,
  2-hydroxy-4-methoxybenzophenone-5-sulfonate,
  2,4-dihydroxybenzophenone,
  2,2',4,4'-tetrahydroxybenzophenone,
  2,2'-dihydroxy-4,4'dimethoxybenzophenone,
  2-hydroxy-4-n-octoxybenzophenone,
  2-hydroxy-4-methoxy-4'-methoxybenzophenone,
  α-(2-oxoborn-3-ylidene)-tolyl-4-sulfonic acid and soluble salts thereof,
  3-(4'-sulfo)benzyliden-bornan-2-one and soluble salts thereof,
  3-(4'methylbenzylidene)-d,1-camphor,
  3-benzylidene-d,1-camphor,
  benzene 1,4-di(3-methylidene-10-camphosulfonic) acid and salts thereof (the product Mexoryl SX described in U.S. Pat. No. 4,585,597 issued to Lang et al. on Apr. 29, 1986),
  urocanic acid,
  2,4,6-tris[p-(2'-ethylhexyl-1'-oxycarbonyl)-anilinol-1,3,5-triazine,
  2-[(p-(tertiobutylamido)anilino]-4,6-bis-[(p-(2'-ethylhexyl-1'-oxycarbonyl)anilino]-1,3,5-triazine,
  2,4-bis{[4-(2-ethyl-hexyloxy)]-2-hydroxy]-phenyl}-6-(4-methoxy-phenyl)-1,3,5-triazine ("TINOSORB S" marketed by Ciba),
  the polymer of N-(2 et 4)-[(2-oxoborn-3-yliden)methyl]benzyl]-acrylamide,
  1,4-bisbenzimidazolyl-phenylen-3,3',5,5'-tetrasulfonic acid and salts thereof,
  the benzalmalonate-substituted polyorganosiloxanes,
  the benzotriazole-substituted polyorganosiloxanes (Drometrizole Trisiloxane),
  dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that marketed under the trademark TINOSORB M by Ciba-Geigy, and
  solubilized 2,2'-methylene-bis-[6-(2H-benzotriazol-2-yl)-4-(methyl)phenol] such as that marketed under the trademark MIXXIM BB/200 by Fairmount Chemical.

Typically preferred among the subject sunscreens are one or more of the following: avobenzone, octyl salicylate, octocrylene, and oxybenzone. Combinations of one of more of these sunscreens is similarly preferred.

The dibenzoyl methane derivatives other than avobenzone are also preferred sunscreens according to the present invention. These are described, for example, in FR-2,326,405, FR-2,440,933 and EP-0,114,607, hereby expressly incorporated by reference.

More preferred dibenzoyl methane sunscreens other than avobenzone include (whether singly or in any combination):
  2-methyldibenzoylmethane
  4-methyldibenzoylmethane
  4-isopropyldibenzoylmethane
  4-tert.-butyldibenzoylmethane
  2,4-dimethyldibenzoylmethane
  2,5-dimethyldibenzoylmethane
  4,4'-diisopropyldibenzoylmethane
  4,4'-dimethoxydibenzoylmethane
  2-methyl-5-isopropyl-4'-methoxydibenzoylmethane
  2-methyl-5-tert.-butyl-4'-methoxydibenzoylmethane
  2,4-dimethyl-4'-methoxydibenzoylmethane
  2,6-dimethyl-4-tert.-butyl-4'-methoxydibenzoylmethane The subject at least one UV-A and/or UV-B sunscreen is advantageously formulated into the compositions of the invention in amounts ranging from about 0.01% to about 30%, and preferably from about 0.1% to about 25%, by weight thereof. Of course, depending upon the nature of the particular formulation, higher or lower amounts may be suitable.

Thus, the present invention features topically applicable cosmetic/dermatological sunscreen compositions, preferably alcoholic sunscreen gels, comprising both at least one UV-A and/or UV-B sunscreen and an effective film-forming and non-pilling amount of an acrylates/$C_{12-22}$ alkylmethacrylate copolymer, preferably a tetrapolymer of methacrylic acid, methyl methacrylate, butyl acrylate and cetyl-eicosinyl methacrylate, formulated into a topically applicable, cosmetically/dermatologically acceptable vehicle, diluent or carrier therefor.

Concordantly, this invention features a regime or regimen for photoprotecting human skin, hair and/or scalp against the damaging or deleterious effects of ultraviolet irradiation, comprising topically applying onto the skin, hair and/or scalp of a human subject, a cosmetic/dermatological composition which comprises (a) an effective UV-photoprotecting amount of at least one UV-A and/or UV-B sunscreen, and (b) an effective film-forming and non-pilling amount of an acrylates/$C_{12-22}$ alkylmethacrylate copolymer, notably a tetrapolymer of methacrylic acid, methyl methacrylate, butyl acrylate and cetyl-eicosinyl methacrylate.

Also featured hereby are concordantly UV-photoprotecting and artificial or sunless tanning compositions comprising those constituents (a) and (b) as indicated above, together with an effective amount of at least one artificial/sunless tanning agent, notably dihydroxyacetone or DHA.

To date, a wide variety of artificial tanning agents has been developed. Artificial tanners provide the highly sought-after tanning or darkening response once only available through harmful exposure to ultraviolet radiation. DHA, in particular, has been widely utilized in cosmetics to accomplish artificial tanning of the skin. Proteins of the epidermis have a very high concentration of arginine, lysine, and histidine and the reaction of skin with DHA to produce an artificial tan takes advantage of this fact. The tanning reaction proceeds through combination with free amino groups in skin proteins, and particularly by combination of DHA with the free guanido group in arginine.

Preferred among those artificial tanners which are useful in the compositions of the instant invention are those selected from the group comprising: allose, alpha hydroxy substituted ketones such as dihydroxyacetone, altrose, arabinose, erythrose, fructose, galactose, glucose, glyceraldehyde, indoles, lactose, mannose, reose, ribose, pentose, sucrose, tallose, xylose, and mixtures thereof.

Most preferred among these artificial/sunless tanners which are useful in the compositions of the present inventions is dihydroxyacetone.

A wide variety of additional components can be employed in the topical cosmetic/dermatological compositions herein. The compositions of the present invention can comprise a safe and effective amount of a pharmaceutical additive or adjuvant. The phrase "safe and effective" connotes an amount of an active agent high enough to significantly or positively modify the condition to be treated, but low enough to avoid serious side effects (at a reasonable benefit/risk ratio) within the scope of sound medical judgment. A safe and effective amount of the pharmaceutical active agent will vary with the specific active species, the ability of the composition to penetrate the active species through the skin, the amount of composition to be applied, the particular condition being treated, the age and physical condition of the patient being treated, the severity of the condition, the duration of the treatment, the nature of concurrent therapy, and like factors.

Useful pharmaceutical active agents which may be conjointly administered according to the present invention include antimicrobial drugs: antibacterials, antifungals, antiprotozoans, and antivirals. Antimicrobial drugs preferred for inclusion in compositions of the present invention comprise pharmaceutically acceptable salts of β-lactam drugs, amanfadine, amikacin, capreomycin, chlorhexidine, chlortetracycline, ciprofloxacin, clindamycin, doxycycline, erythromycin, ethambutol, gentamicin, kanamycin, lineomycin, methacycline, methenamine, metronidazole, miconazole, minocycline, neomycin, netilmicin, norfloxacin, oxytetracycline, paramomycin, pentamidine, quinolone drugs, streptomycin, tetracycline, tobramycin, and triclosan.

A variety of additional components can be incorporated into the subject cosmetic/dermatological compositions. Non-limiting examples of these additional components include cationic polymers and thickeners, chelators, gums and thickeners, low pH thickening agents, other polymers and materials for enhancing the film-forming and waterproofing properties and substantivity of the composition, sequestrants, skin penetrating aids, suspending agents, vitamins and derivatives thereof, preservatives and aesthetic components.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

The following ethanolic sunscreen gel containing about 2% by weight active Allianz OPT was formulated:

| Phase | Ingredient | % |
|---|---|---|
| A1 | SD Alcohol 40-2 | to 100% |
|  | Emollient | 8 |
|  | Avobenzone | 3 |
|  | Octocrylene | 10 |
|  | Oxybenzone | 6 |
|  | Octyl Salicylate | 5 |
| A2 | Allianz OPT | 4.2 (for 2% active level) |
| A3 | Hydroxypropyl cellulose | 2 |

The components of phase A1 were combined in a main kettle. Mixing was achieved using an overhead mixer with a propeller blade. The components were mixed until all of the sunscreens were solubilized. The component of phase A2 (Allianz OPT) was added to the kettle, and mixed until the polymer was dispersed homogeneously, about 15–20 minutes. The mixture was cloudy, but homogeneous. Next, the component of phase A3 (hydroxypropyl cellulose) was slowly added to the kettle. The batch was mixed for approximately 1 hour to disperse the hydroxypropyl cellulose. The batch thickened until a gel was formed.

EXAMPLE 2

The ethanolic sunscreen gel formulation of Example 1, containing about 2% by weight of active Allianz OPT, was compared to a like formulation, but containing a corresponding amount by weight of Dermacryl LT instead of the Allianz OPT, in a sensory study by eight (8) sensory expert panelists trained and skilled in the evaluation and techniques for skin care products.

The purpose of this sensory study was to determine any differences in the application, kinesthetic, visual and tactile attributes between the two sunscreens.

The protocol for the study, the standard skin feel protocol to assess all skin attributes, was as follows:

1. Panelists used a standard cleaner to wash their arms before product application and allowed their skin to equilibrate for 10 minutes.

2. Then 1 cc of each product was applied to each lower arm. The Dermacryl LT formulation was applied to the lower right arm and the Allianz OPT formulation according to the invention was applied to the lower left arm.

3. Using the 25-rotation method, panelists determined the type of spread within the first 5 rotations, and whether there was an initial and/or complete absorption by the $25^{th}$ rotation.

4. The panelists continued to rotate the products on their arms until the $40^{th}$ rotation to determine if the respective products produced pilling.

5. Immediately after spreading the product, panelists answered a questionnaire related to the application, kinesthetic, visual and tactile performance of each product. At 1, 3 and 5 minutes from the time of application, panelists answered a tack question.

6. The panelists re-applied the respective products to the exact same places on their arms 10 minutes after the first application. The panelists rotated the products on their arms for 40 rotations to determine if re-application would cause soaping/whitening and/or pilling.

7. Immediately after this second spreading of the respective products, panelists answered a questionnaire related to the soaping/whitening and pilling produced by the formulations.

It should be appreciated that this sensory test was carried out on a first day (at 74.0° F. and 29.6% relative humidity) and then repeated on the next day (at 72.1° F. and 15.8% relative humidity).

It was thus determined that significant differences existed between the two sunscreen formulations in terms of visual thickness, spreadability and amount of pilling. Both products were considered moderately thick; however, the Allianz OPT formulation was thicker. For spreadability, the Allianz OPT product had slightly less slip than the Dermacryl LT product. Pilling occurred with the Dermacryl LT product and none with the Allianz OPT product. Scores for absorption indicated both formulations initially absorbed into the skin between 15 and 16 rotations. The range of complete absorption for both products was between 22 and 23 rotations. Only one panelist experienced whitening with the Dermacryl LT formulation and none with the Allianz OPT formulation.

And as regards the re-application attributes, there were significant differences observed between the two products in terms of amount of pilling. There was no pilling experienced with the Allianz OPT product of the invention (0.00) as compared with that amount experienced with the Dermacryl LT product (3.81). None of the panelists experienced soaping/whitening with either product.

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, non-pilling UV-photoprotecting cosmetic/dermatological sunscreen composition comprising an effective amount of at least one UV-A and/or UV-B screening agent and an effective non-pilling amount of an acrylates/$C_{12-22}$ alkylmethacrylate copolymer, formulated into a topically applicable, cosmetically/dermatologically acceptable vehicle, diluent or carrier therefor, said composition being formulated as an alcoholic sunscreen gel.

2. The non-pilling UV-photoprotecting sunscreen composition as defined by claim 1, said acrylates/$C_{12-22}$ alkylmethacrylate copolymer comprising a tetrapolymer of methacrylic acid, methyl methacrylate, butyl acrylate and cetyl-eicosinyl methacrylate.

3. The non-pilling UV-photoprotecting sunscreen composition as defined by claim 1, further comprising an effective self-tanning amount of at least one artificial/sunless tanning agent.

4. The non-pilling UV-photoprotecting sunscreen composition as defined by claim 3, said at least one artificial/sunless tanning agent comprising dihydroxyacetone.

5. The non-pilling UV-photoprotecting sunscreen composition as defined by claim 1, further comprising at least one antibacterial, antifungal, antiprotozoan and/or antiviral active agent.

6. The non-pilling UV-photoprotecting sunscreen composition as defined by claim 1, further comprising at least one conventional cosmetic/dermatological additive and/or adjuvant.

7. The non-pilling UV-photoprotecting sunscreen composition as defined by claim 1, said at least one UV-A and/or UV-B screening agent comprising avobenzone, octocrylene, oxybenzone and/or octyl salicylate.

8. The non-pilling UV-photoprotecting sunscreen composition as defined by claim 1, comprising from about 0.25% to about 5% by weight of said acrylates/$C_{12-22}$ alkylmethacrylate copolymer.

9. The non-pilling UV-photoprotecting sunscreen composition as defined by claim 8, comprising from about 1% to about 5% by weight of said acrylates/$C_{12-22}$ alkylmethacrylate copolymer.

10. The non-pilling UV-photoprotecting sunscreen composition as defined by claim 8, comprising from about 0.01% to about 30% by weight of said at least one UV-A and/or UV-B screening agent.

11. The non-pilling UV-photoprotecting sunscreen composition as defined by claim 10, comprising from about 1% to about 25% by weight of said at least one UV-A and/or UV-B screening agent.

12. A regime or regimen for UV-photoprotecting human skin and/or hair against the damaging and deleterious effects of ultraviolet irradiation, comprising topically applying thereon a non-pilling UV-photoprotecting cosmetic/dermatological sunscreen composition which comprises an effective amount of at least one UV-A and/or UV-B screening agent and an effective non-pilling amount of an acrylates/$C_{12-22}$ alkylmethacrylate copolymer, formulated into a topically applicable, cosmetically/dermatologically acceptable vehicle, diluent or carrier therefor, said composition being formulated as an alcoholic sunscreen gel.

13. A regime or regimen for UV-photoprotecting human skin and/or hair against the damaging and deleterious effects of ultraviolet irradiation, comprising topically applying thereon a non-pilling UV-photoprotecting cosmetic/dermatological sunscreen composition which comprises an effective amount of at least one UV-A and/or UV-B screening agent and an effective non-pilling amount of a tetrapolymer of methacrylic acid, methyl methacrylate, butyl acrylate and cetyl-eicosinyl methacrylate, formulated into a topically applicable, cosmetically/dermatologically acceptable vehicle, diluent or carrier therefor, said composition being formulated as an alcoholic sunscreen gel.

14. The non-pilling UV-photoprotecting sunscreen composition as defined by claim 2, said at least one UV-A and/or UV-B screening agent comprising avobenzone, octocrylene, oxybenzone and/or octyl salicylate.

15. A topically applicable, non-pilling UV-photoprotecting cosmetic/dermatological sunscreen composition comprising an effective amount of at least one UV-A and/or UV-B screening agent and effective non-pilling amount of a tetrapolymer of methacrylic acid, methyl methacrylate, butyl acrylate and cetyl-eiconsinyl methacrylate, formulated into a topically applicable, cosmetically/dermatologically acceptable vehicle diluent or carrier therefor.

16. The non-pilling UV-photoprotecting sunscreen composition as defined by claim 15, said at least one UV-A and/or UV-B screening agent comprising avobenzone, octocrylene, oxybenzone and/or octyl salicylate.

17. A regime or regimen for UV-photoprotecting human skin and/or hair against the damaging and deleterious effects of ultraviolet irradiation, comprising topically applying thereon a non-pilling UV-photoprotecting cosmetic/dermatological sunscreen composition which comprises an effective amount of at least one UV-A and/or UV-B screening agent and an effective non-pilling amount of a tetrapolymer of methacrylic acid, methyl methacrylate, butyl acrylate and cetyl-eicosinyl methacrylate, formulated into a topically applicable, cosmetically/dermatologically acceptable vehicle, diluent or carrier therefor.

* * * * *